United States Patent
Ikeda (10) Patent No.: US 8,852,957 B2
(45) Date of Patent: Oct. 7, 2014

(54) MAGNETIC MATERIAL SENSOR AND DETECTION METHOD EMPLOYING THIS SENSOR, AND TARGET MATERIAL DETECTION SENSOR AND TARGET MATERIAL DETECTION KIT

(75) Inventor: Takashi Ikeda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1048 days.

(21) Appl. No.: 11/720,516

(22) PCT Filed: Jan. 26, 2006

(86) PCT No.: PCT/JP2006/301714
§ 371 (c)(1),
(2), (4) Date: May 30, 2007

(87) PCT Pub. No.: WO2006/080558
PCT Pub. Date: Aug. 3, 2006

(65) Prior Publication Data
US 2008/0284419 A1    Nov. 20, 2008

(30) Foreign Application Priority Data

Jan. 31, 2005 (JP) ................................. 2005-023518

(51) Int. Cl.
| | |
|---|---|
| G01N 33/533 | (2006.01) |
| G01R 33/12 | (2006.01) |
| G01N 15/06 | (2006.01) |
| G01R 33/09 | (2006.01) |
| B82Y 25/00 | (2011.01) |
| G01N 35/00 | (2006.01) |

(52) U.S. Cl.
CPC ........ *G01N 15/0656* (2013.01); *G01R 33/1269* (2013.01); *G01R 33/093* (2013.01); *G01R 33/1284* (2013.01); *G01R 33/09* (2013.01); *G01R 33/12* (2013.01); *G01N 35/0098* (2013.01); *B82Y 25/00* (2013.01); *Y10S 436/806* (2013.01)
USPC ................. 436/526; 435/287.2; 436/806

(58) Field of Classification Search
None
See application file for complete search history.

(56) References Cited

U.S. PATENT DOCUMENTS

| | | | |
|---|---|---|---|
| 5,923,637 | A | 7/1999 | Shimada et al. |
| 5,981,297 | A | 11/1999 | Baselt |

(Continued)

FOREIGN PATENT DOCUMENTS

| | | | |
|---|---|---|---|
| JP | 3223685 | A | 10/1991 |
| JP | 2001358379 | A | 12/2001 |
| JP | 2002299725 | A | 10/2002 |
| JP | 2004205495 | A | 7/2004 |
| JP | 2004289100 | | 10/2004 |

OTHER PUBLICATIONS

D. L. Graham, et al., "High Sensitivity Detection of Molecular Recognition Using Magnetically Labelled Biomolecules and Magnetoresistive Sensors", Biosensors and Bioelectronics, 2003, vol. 18, pp. 483-488.

(Continued)

*Primary Examiner* — Chris L Chin
*Assistant Examiner* — Richard Moerschell
(74) *Attorney, Agent, or Firm* — Fitzpatrick, Cella, Harper & Scinto (57) ABSTRACT

The present invention provides an appropriately produced magnetic material sensor having a small size.

The magnetic material sensor of this invention includes: a magnetoresistive effect film, formed using magnetic films; a current source, for supplying to the magnetoresistive effect film a current having a magnitude and a direction that can change the magnetization directions of the magnetic films; and a detector, for detecting the resistance of the magnetoresistive effect film.

10 Claims, 5 Drawing Sheets

(56) References Cited

U.S. PATENT DOCUMENTS

| | | | |
|---|---|---|---|
| 6,468,809 B1* | 10/2002 | Prinz et al. | 436/526 |
| 7,031,186 B2 | 4/2006 | Kang et al. | |
| 7,048,890 B2* | 5/2006 | Coehoorn et al. | 422/82.02 |
| 7,221,583 B2 | 5/2007 | Ikeda | |
| 2003/0030945 A1* | 2/2003 | Heinonen et al. | 360/324.2 |
| 2004/0120185 A1 | 6/2004 | Kang et al. | |
| 2006/0226832 A1 | 10/2006 | Ikeda et al. | |
| 2007/0290683 A1 | 12/2007 | Ikeda et al. | |

OTHER PUBLICATIONS

J. C. Slonczewski, "Current-driven Excitation of Magnetic Multilayers", Journal of Magnetism and Magnetic Materials, Letter to the Editor, 1996, vol. 159, pp. L1-L7.

L. Berger, "Emission of Spin Waves by a Magnetic Multilayer Traversed by a Current", The American Physical Society, 1996, vol. 54, No. 13, pp. 9353-9358.

* cited by examiner

MAGNETIC MATERIAL SENSOR AND DETECTION METHOD EMPLOYING THIS SENSOR, AND TARGET MATERIAL DETECTION SENSOR AND TARGET MATERIAL DETECTION KIT

TECHNICAL FIELD

The present invention relates to a magnetic material sensor and a detection method employing this sensor, and a target material detection sensor and a target material detection kit.

BACKGROUND ART

Many technologies, such as radio immunoassay (RIA or IRMA: immunoradiometric assay) and enzyme-antibody technique, have been proposed and employed for immunization analysis. According to radio immunoassay, a competitive antigen or an antibody is marked using a radionuclide, and a fixed quantity of the antigen is measured, based on the results of a specific activity. For this method, high sensitivity is an advantage; however, there is a problem as regards the security of the radionuclide, and therefore, a special facility and a special apparatus are required. Further, compared with radio immunoassay, enzyme-antibody technique, which employs an enzyme that is used to mark an antibody, is easier operationally, and satisfies requirements for practical sensitivity; however, there is a continuing demand for more sensitivity and increased operational usability.

Under these circumstances, recently, D. L. Graham, et al., Biosensors & Bioelectronics 18, 483 (2003) proposed a method whereby, in order to easily detect a target material, magnetic particles coupled to the target material are detected by employing a magnetoresistive effect film.

According to the technique disclosed in this reference document, two GMR (Giant Magnetic Resistance effect) films of 2 μm×6 μm are employed to detect magnetic particles having a diameter of 2 μm. Bithion is coupled with the surface of one of the GMR films, to immobilize magnetic particles, but is not coupled with the surface of the other GMR film. Further, the magnetic particles are avidin-modified. Since avidin and bithion are very strongly coupled, magnetic particles are immobilized on one of the GMR films, while on the other GMR film, none are immobilized. Since the magnetized state of the GMR film whereat the magnetic particles are immobilized is changed by the effect produced by a floating magnetic field generated by a magnetic particle, the resistance of this GMR film differs from the other GMR film, whereon no magnetic particles are immobilized. For the GMR films, a multi-layer structure, comprising two magnetic films, between which a non-magnetic metal film is formed, is employed as a basic structure. The resistance value depends on the relative magnetization directions of the two magnetic films, and characteristically, when the magnetization directions are parallel there is comparatively little resistance, but when the magnetization directions are antiparallel there is a comparatively large resistance. In order to provide the parallel magnetized state and the antiparallel magnetized state, the two GMR magnetic films are formed of a magnetic material having a coercive force, such that inversion of the magnetization direction of one of the magnetic films is difficult, and inversion of the magnetization direction of the other magnetic film is enabled by a floating magnetic field generated by a magnetic particle.

Figure 9:
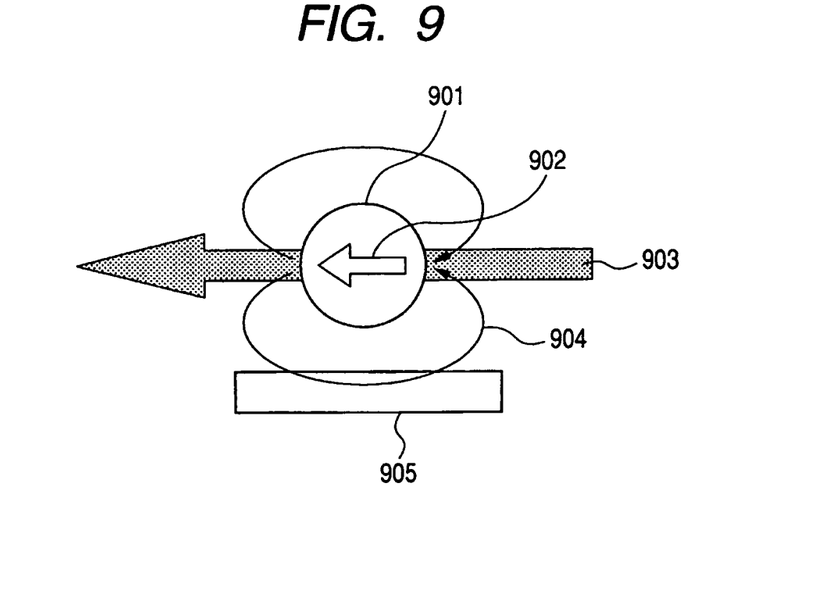
FIG. 9 is a conceptual diagram for explaining the direction of a floating magnetic field generated by a magnetic particle.

When a magnetic field is applied to magnetic particles and the GMR films in the in-plane direction, and when a magnetization direction 902 of the magnetic particles is directed toward the applied magnetic field, as shown in FIG. 9, a floating magnetic field 904 generated by a magnetic particle 901 is applied to a GMR film 905 in a direction opposite to that in which a magnetic field 903 is to be applied. Therefore, the magnetization directions of the two magnetic films composing the GMR film do not become parallel. On the other hand, since the magnetic films of a GMR film whereon magnetic particles are not immobilized are not affected by the floating magnetic field, the magnetization directions are parallel across the entire film. That is, since the magnetized states of the two GMR films differ, a further difference occurs between the resistances, so that the detection of magnetic particles is enabled.

As described above, the magnetic particle detection method employing the GMR films is performed by magnetizing magnetic particles in a desired direction, and by changing the magnetization direction of a magnetoresistive effect film using a floating magnetic field generated by magnetic particles. Using this method, magnetic particles can easily be detected.

In the description of the previous reference document, a detection signal for a magnetic particle obtained by one GMR film differs from that obtained by another, and depends on the number of magnetic particles. This occurs because the size of the area on GMR film that is influenced by a floating magnetic field, generated by a magnetic particle, differs in accordance with the number of magnetic particles. However, when relative to the total area of the GMR film the ratio of the area influenced by a floating magnetic field, generated by a magnetic field, is considerably smaller, a remarkably weak detection signal is obtained, and the detection of magnetic particles is impossible. Therefore, in order to obtain a strong detection signal, the size of the GMR film should be consonant with the sizes of the magnetic particles.

At present, of the commonly employed magnetic particles, a small magnetic particle size is several tens of nm in diameter. In order to detect such a small magnetic particle, it is preferable that a GMR film of the same size, i.e., about several tens of nm, be employed, while taking into account the area affected by a floating magnetic field generated by a magnetic particle. However, when the size of the magnetic film is reduced, the inversion of the magnetization direction becomes more difficult, and the detection signal produced by a magnetic particle is weakened.

Furthermore, since means required to apply a uniform magnetic field to an area for the detection of a magnetic material must be large, the production of a compact sensor is not easy.

DISCLOSURE OF THE INVENTION

To resolve these shortcomings, the objective of the present invention is to provide a magnetic material sensor that can be compactly produced and that can be employed, for a magnetoresistive effect film, to detect a magnetic material that enables the magnetization direction of a magnetic film to be changed by supplying a current to the magnetic material sensor, and whereby a change in the voltage of the magnetoresistive effect film, which occurs as a result of the interaction of a magnetic material to be detected and the magnetic film of the sensor, is employed to determine whether the magnetic material is present or absent, as well as the number of magnetic materials.

Specifically, a magnetic material sensor according to the present invention comprises:

a magnetoresistive effect film, formed using magnetic films;

a current source, for supplying, to the magnetoresistive effect film, a current having a magnitude and a direction that enables the changing of a magnetized state of the magnetic films; and a detector, for detecting a resistance of the magnetoresistive effect film.

Further, according to this invention, a detection method, for employing a magnetic material sensor that includes a magnetoresistive effect film that is formed of a detection layer, which is a magnetic film for which the magnetization direction is changed by the reception of a current in a perpendicular direction, a magnetized pinned layer, which is a magnetic film for which the magnetization direction is not changed by the reception of the current, and a non-magnetic layer, which is formed between the detection layer and the magnetized pinned layer, comprises the steps of:

supplying a current to the magnetoresistive effect film to change a magnetized state of the detection layer; and detecting a change in resistance at the magnetoresistive effect film to determine whether a magnetic material is present or absent and to determine the number of magnetic materials.

A target material detection sensor according to the present invention immobilizes a magnetic material, through a target material to be detected, in a desired area of one of a number of magnetic material sensors described above, and detects this target material.

A target material detection kit according to the present invention includes: the above described target material detection sensor and a magnetic particle modified by a material that is specifically coupled with a target material.

Other features and advantages of the present invention will be apparent from the following description taken in conjunction with the accompanying drawings, in which like reference characters designate the same or similar parts throughout the figures thereof.

The accompanying drawings, which are incorporated in and constitute a part of the specification, illustrate embodiments of the invention and, together with the description, serve to explain the principles of the invention.

BEST MODE FOR CARRYING OUT THE INVENTION

As described above, a GMR film comprises two magnetic films, and the magnetization direction of one of the magnetic films tends to face the external magnetic field, while the magnetization direction of the other magnetic film is not easily inverted. An example magnetic film, the magnetization of which tends to be directed toward the external magnetic field, is NiFe; however, since the magnetoresistivity of this film is small, a NiFeCo film or an exchange coupling film of NiFe and FeCo is frequently employed. When the exchange coupling film is employed, a FeCo film that induces a large magnetoresistivity is positioned so it contacts a non-magnetic material such as Cu, which is formed between two magnetic materials, and the magnetoresistivity is the rate of a resistance that is changed when the magnetization directions of two magnetic films are shifted from parallel to antiparallel. That is, as the magnetoresistivity becomes greater, a stronger detection signal is obtained.

As another magnetoresistive effect film, other than a GMR film, there is a TMR (Tunneling Magnetic Resistance effect) film. As the basic structure of the TMR film, the non-magnetic metal film of the GMR film is replaced with a thin dielectric film, and a current to be detected is supplied in a direction perpendicular to the surface of the TMR film, so that electrons tunnel through the dielectric film. Compared with the GMR film, the TMR film has a greater magnetoresistivity and a larger resistance. Therefore, the TMR film is little affected by wiring resistance, and is appropriate as a sensor employing a large-scale integrated circuit. $Al_2O_3$ or MgO is generally employed as a dielectric film used for the TMR film.

As characteristics, the two magnetic films of the magnetoresistive effect film are affected by magnetostatic coupling that acts on the interface, and it is highly doubtful that the magnetization directions of the films will become antiparallel. Therefore, when the difference in the coercive forces of the two magnetic films is small, it is difficult for that magnetization to become antiparallel, and as a result, a large magnetoresistance can not be obtained.

Thus, a magnetoresistive effect film of a spin-valve type is proposed for which, in order to provide an antiparallel state, an antiferromagnetic film is exchange coupled with a magnetic film, the magnetization direction of which is to be immobilized. The antiferromagnetic film is a magnetic material for which there is an apparent magnetization direction because adjacent faces spin in opposite directions, and the spin directions are not inverted by applying a large magnetic field. Therefore, when a ferromagnetic film is exchange coupled with an antiferromagnetic film, the spinning of the antiferromagnetic film must be inverted for magnetization of the ferromagnetic film, so that magnetization inversion seldom occurs. MnIr, MnPt, MnFe, NiO or FeS can be employed as the antiferromagnetic film, and further, an artificial antiferromagnetic film, wherein a non-magnetic thin film is sandwiched between two ferromagnetic films, may also be employed.

In an artificial antiferromagnetic film, two ferromagnetic films have a strong interaction, and the magnetization directions are antiparallel.

Figure 10A:
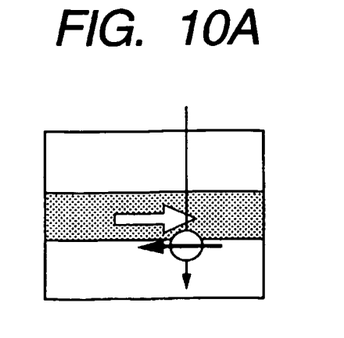
FIGS. 10A and 10B are conceptual diagrams for explaining an inversion of magnetization due to spin-injection, respectively showing the state before the inversion of magnetization and the state following the inversion of magnetization.
Figure 10B:
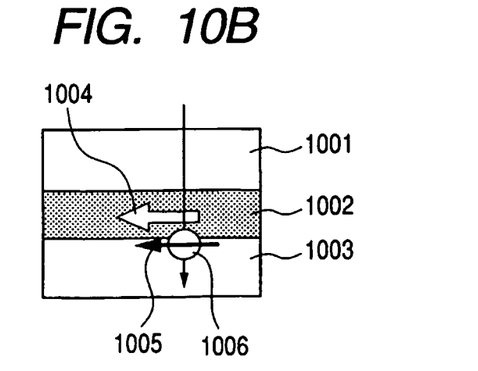

The application of a magnetic field is widely employed in order to invert the magnetization of a magnetic material. Recently, a method (a spin-injection method) has been proposed whereby the magnetization direction is changed by supplying a spin-polarized current to a magnetic material (e.g., J. C. Slonczewski: J. Magn. Mat., 159, L1 (1996), L. Berger: Phys. Rev. B, 54, 9353 (1996)). According to this method, as shown in FIG. 10A, an electron 1006, having a magnetization vector 1004 aligned to the right, and a spin vector 1005, which is aligned to the left, are supplied to a magnetic material that is formed of a non-magnetic film 1001, a magnetic film 1002 and a non-magnetic film 1003. The interaction of the spin vector 1005 and the magnetization vector 1006 is induced near the surface of the magnetic film 1002, and as shown in FIG. 10B, the magnetization direction of the magnetic film is aligned with the direction of the spin vector 1005. When this magnetization inversion method is employed for a magnetic material sensor, a strong detection signal can be obtained from a small magnetic particle, and the reduction in size of the sensor can be performed Further, as shown in FIGS. 11A to 11D, a detection layer 1101, a non-magnetic layer 1103 and a magnetized pinned layer 1104 are formed between a non-magnetic layer 1101 and a non-magnetic layer 1105, and a power source 1109 for applying a voltage to the non-magnetic layers 1101 and 1105 is positioned so that the magnetization direction can be arbitrarily changed. It should be noted that the thickness of one of the magnetic films should be smaller than a spin diffusion length, and the thickness of the other magnetic film should be greater than the spin diffusion length. This spin diffusion length differs in accordance with the material, or the structure, of the film, and in this case, a thinner magnetic material is used for the detection layer 1102, and the other magnetic material is the magnetized pinned layer 1104.

Figure 11A:
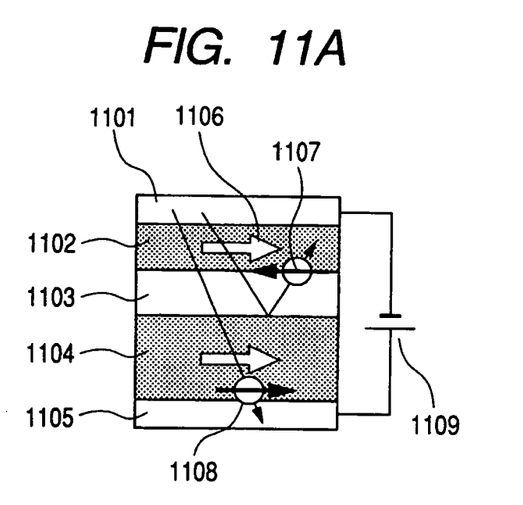
FIGS. 11A, 11B, 11C and 11D are conceptual diagrams for explaining an inversion of magnetization due to spin-injection, respectively showing the state before the inversion of magnetization, when electrons are injected from a detection layer side, the state following the inversion of magnetization, when electrons are injected from the detection layer side, the state before the inversion of magnetization, when electrons are injected from a magnetized pinned layer side, and the state following the inversion of magnetization, when electrons are injected from the magnetized pinned layer side.
Figure 11B:
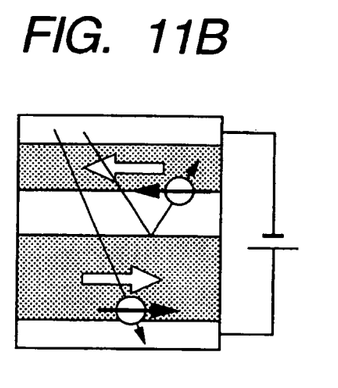

Assume that initially, as shown in FIG. 11A, the magnetization directions of two magnetic films (the detection layer 1102 and the magnetized pinned layer 1104) are parallel, and that electrons 1108 are injected from above the multi-layer film, i.e., from the detection layer 1102 side. The injected electrons 1108 pass through the detection layer 1102 and then reach the magnetized pinned layer 1104. Then, the electrons 1108 having a spin parallel to the magnetization direction pass through the magnetized pinned layer 1104, while the electrons 1108 having an antiparallel spin are reflected by the magnetized pinned layer 1104 and produce an exchange interaction with the magnetization of the detection layer 1102. Therefore, the magnetization direction of the detection layer 1102 is aligned with the direction of a spin vector 1107 that is generated by the electrons 1108 reflected by the magnetized pinned layer 1104, and is inverted as shown in FIG. 11B.

Figure 11C:
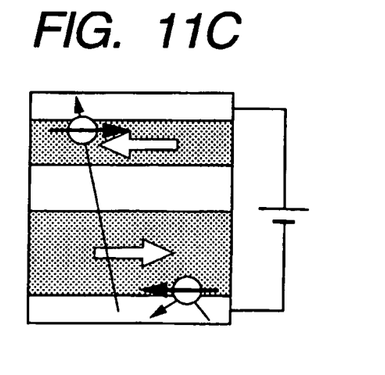
Figure 11D:
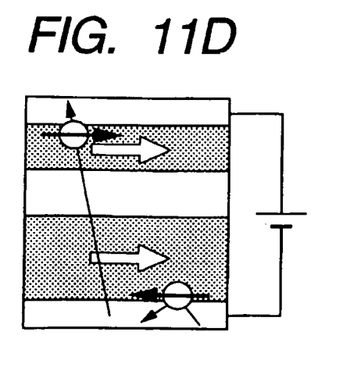

When, as shown in FIG. 11C, the direction of a current that is supplied by the power source 1109 is reversed, the injected electrons 1108 that have a spin parallel to the magnetization direction of the magnetized pinned layer 1104 pass through the magnetized pinned layer 1104 and produce an exchange interaction with the magnetization of the detection layer 1102. On the other hand, the electrons 1108 having an antiparallel spin are reflected by the magnetized pinned layer 1104. And therefore, the magnetization of the detection layer 1102 shown in FIG. 11C is aligned with the magnetization direction of the magnetized pinned layer 1104, as shown in FIG. 11D. That is, the magnetization direction of the detection layer 1102 can be controlled by using a direction corresponding to that in which a current flows.

According to the spin-injection magnetization inversion method described above, the magnitude of a current required for the inversion of magnetization depends on the volume of the magnetic material, and as the volume is reduced, the magnitude of the current can also be reduced. That is, when the spin-injection magnetization inversion method is employed for a small magnetoresistive effect film, only a small current is required to provide control for the magnetization direction.

Figure 1:
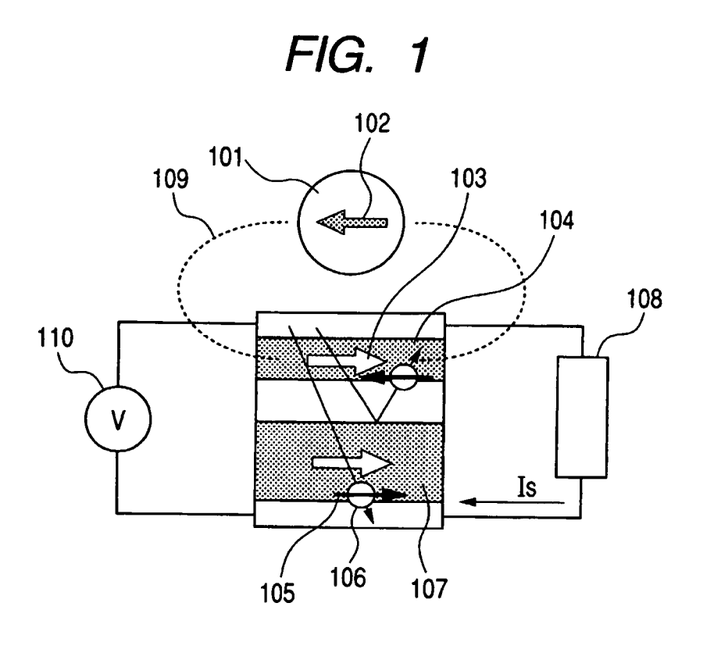
FIG. 1 is a conceptual diagram for explaining the principle of a magnetic material sensor according to the present invention.

FIG. 1 is a schematic block diagram showing an example arrangement for a magnetic material sensor according to the present invention. The magnetic material sensor for this invention, as well as that shown in FIGS. 11A to 11D, comprises: two magnetic layers, i.e., a detection layer 104 and a magnetized pinned layer 107; and a non-magnetic layer. Also as shown in FIG. 1, a power source 108 and a voltage detector 110, for detecting a voltage to be applied to both ends of a magnetoresistive effect film, are connected to the magnetic material sensor. In this case, assume that the two magnetic layers are in-plane magnetized films and the magnetization directions of the two magnetic films are parallel. The detector 110 is not limited to a voltage detector, and any detection device can be employed that can detect a change in the resistance of a magnetoresistive effect film.

When electrons 106 are injected from the detection layer 104 side, as the strength of a current is gradually increased, magnetization is inverted by a spin vector 105 at a specific current value. It should be noted that this current value will differ, depending on whether a magnetic particle 101 is present near the magnetic material sensor. This is true because when a magnetic particle 101 is present near the magnetic material sensor, a magnetostatic coupling 109 exists between the detection layer 104 and the magnetic particle 101. If, as shown in FIG. 1, a magnetization vector 103 of the detection layer 104 and a magnetization vector 102 of the magnetic particle 101 are antiparallel to each other, and stable, the magnetization direction of the magnetic particle 101 must be inverted in order for the magnetization direction of the detection layer 104 to be inverted, and an extra current is required that corresponds to the energy required for the inversion of the magnetization of the magnetic particle 101.

Figure 2:
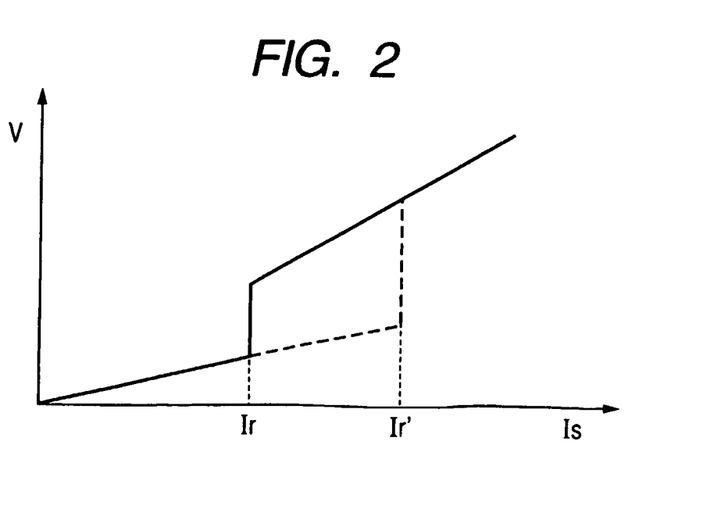
FIG. 2 is a graph showing the relationship of a current to be supplied to the magnetic material sensor of the present invention and a voltage to be applied to the magnetic material sensor.

Therefore, there is a difference, as shown in FIG. 2, between the voltage that is detected when the magnetic particle 101 is present and the voltage that is detected when it is not. In FIG. 2, a solid line indicates a relationship between the current and the voltage when the magnetic particle 101 is not present, and Ir denotes a critical current at which magnetization inversion is enabled. A broken line indicates a relationship between the current and the voltage when the magnetic particle 101 has been preset, while Ir' also denotes a critical current at which magnetization inversion is enabled. Since the magnetization directions of the two magnetic layers become antiparallel through the inversion of the magnetization, the resistance at the magnetic material sensor is increased and a high voltage is detected.

Figure 3:
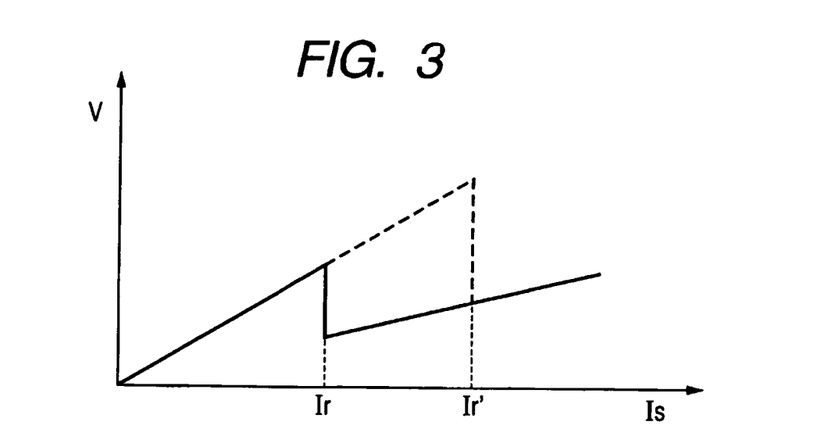
FIG. 3 is a graph showing the relationship of a current to be supplied to the magnetic material sensor of the present invention and a voltage to be applied to the magnetic material sensor.

Furthermore, when the electrons 106 from the magnetized pinned layer 107 are injected under a condition wherein the magnetization directions of the two magnetic layers are antiparallel, the magnetization directions become parallel when the current is equal to or higher than a critical current. Thus, the relationship between the voltage and the current is as shown in FIG. 3.

Therefore, by examining the relationship between the voltage and the current, it is possible to determine whether a magnetic material is present near the magnetic material sensor.

Any type of magnetic material can be employed for this invention so long as the magnetization of the material can be inverted by spin injection and the material can be magnetostatically coupled with another magnetic material. A transition metal, such as Fe, Co or Ni, or an alloy of them, is appropriate, and an easily attained direction of magnetization may be a direction perpendicular to the face of a film, instead of an in-plane direction. A material that can be easily magnetized in the perpendicular direction is, for example, an alloy film or a multi-layer film consisting of a rare-earth metal and a transition metal, an artificial lattice film consisting of a noble metal and a transition metal, a CoCr alloy film, or a Ba ferrite alloy film.

It is preferable that the non-magnetic layer, located between the two magnetic layers, be formed of a material through which electrons can pass, and the spin state can be appropriately kept in. So long as such conditions are satisfied, either a conductive material or a dielectric material may be employed, and Cu, for example, can be employed as a conductive material, while $Al_2O_3$ or MgO can be employed as a dielectric material.

The detection method that employs a direct current has been explained. A magnetic material may be detected by inverting the magnetization direction of the detection layer several times through the employment of an alternating current.

Figure 4:
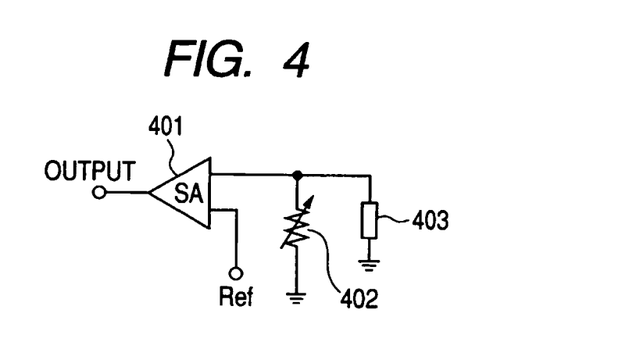
FIG. 4 is a circuit diagram showing the magnetic material sensor of the present invention.

Detection of a magnetic material is performed as shown in FIG. 4, for example, by connecting a sense amplifier (SA) 401 to a magnetoresistive effect film 402, on which magnetic particles can be immobilized, and a power source 403, and performing a comparison using a reference voltage (ref). When a shift in the resistances of devices occurs, the reference voltage will differ from a desired value, and an accurate detection will not be performed. In order to prevent this, there is a method that employs, as a reference voltage, a voltage that is applied to both ends of a magnetoresistive effect film whereon a magnetic material is not immobilized (an interaction does not occur with a magnetic particle that is to be detected).

In order to immobilize magnetic particles, a process for immobilizing magnetic particles is performed on the surface of the magnetoresistive effect film, i.e., a Au film, for example, is deposited. When the surfaces of magnetic particles are modified using thiol, the magnetic particles are immobilized on the surface of the magnetoresistive effect film by Au-thiol coupling.

Further, the magnetic material sensor of this invention may be employed as a biosensor because a strong detection signal can be obtained, even from a small magnetic particle. Antigens as target materials in this case can, for example, be a biomolecule (a protein, a nucleic acid or a saccharide), an allergen, a bacteria and a virus. However, the target materials are not limited to these, and may be others so long as antibodies that specifically recognize these antigens can be immobilized on a magnetoresistive effect film, and a magnetic particle, and an antigen-antibody reaction can be obtained. For example, a single stranded DNA probe may be fixed to the top surface of the magnetoresistive effect film. Then, a solution that contains magnetic particles modified by a specimen DNA, which is a target material, may be dropped on the detector, and only when the DNA probe and the specimen DNA are coupled together, are magnetic particles immobilized on the top of the magnetoresistive effect film. Magnetic particles that are not immobilized are removed from the detector by cleaning, and a magnetic particle measurement is conducted. When the presence of magnetic particles is detected, it is confirmed that the specimen DNA has a desired DNA array.

The DNA detection method has been described; however, detection of an antigen, for example, can also be performed. The primary antibody to be specifically coupled to a desired antigen is immobilized on a magnetoresistive effect film, and thereafter, a specimen solution is dropped onto the detector. When an antigen is present in the specimen, the primary antibody and the antigen are specifically coupled together. Then, the surface of the detector is cleaned to remove unnecessary material from the specimen. A secondary antibody to be specifically coupled with an antigen is fixed to a magnetic particle used for detection, and a solution that contains the magnetic particles is dropped onto the detector. Thereafter, the surface of the detector is cleaned to remove magnetic particles that have not been coupled with the antigen. A measurement is then performed to detect the magnetic particles, and the antigen is indirectly detected. An example reaction of the biosensor of this invention that employs the magnetic material has been explained. However, an avidin-bithion reaction, an antigen-aptamer (an RNA fragment having a specified structure) interaction, a ligand-receptor interaction, a DNA-protein (transcription factor, etc.) interaction or a lectin-saccharide interaction may be employed.

FIRST EMBODIMENT

Figure 5:
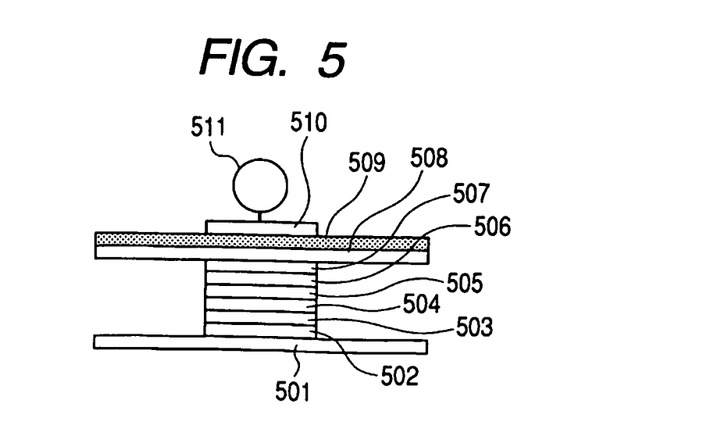
FIG. 5 is a conceptual diagram showing the structure of a magnetoresistive effect film used for the magnetic material sensor of the invention and the positional relationship of this film relative to a magnetic particle.

FIG. 5 is a conceptual diagram showing the structure of a magnetoresistive effect film used for the magnetic material sensor of the present invention, and the positional relationship of the film and a magnetic particle. A TMR film is employed as a magnetoresistive effect film, and a $Al_2O_3$ film is employed as a spin tunnel film 504. Further, an artificial antiferromagnetic film is deposited under the $Al_2O_3$ film and is used as a magnetized pinned layer. The magnetized pinned layer is provided by overlaying, on an lower electrode 501, a MnIr film 502 and a laminated film 503 consisting of a FeCo film, a Ru film and a FeCo film. Since the two FeCo films are magnetically coupled, and the magnetization directions are constantly antiparallel, magnetostatic coupling between the magnetized pinned layer and a detection layer or a magnetic material to be detected is weak. On the $Al_2O_3$ film, an exchange coupling film consisting of a FeCo film 505 and a NiFe film 506 is deposited and is used as a detection layer. Any conductive material can be used for the lower electrode so long as the characteristics of the magnetoresistive effect film are not deteriorated, and in this embodiment, Hf is employed. On the top of the magnetoresistive effect film, a Pt film is formed as a protective film 507 to prevent the corrosion of a magnetic material during the post process. For an upper electrode 508, an arbitrary conductive material can be employed so long as the characteristics of the magnetoresistive effect film are not deteriorated, and in this embodiment, a Pt film is employed. The top of the upper electrode 508 is covered with a SiO$_2$ film that serves as a protective film 509 and is used to prevent the pinned of the thiol group of a magnetic particle. Further, in the area atop that whereat magnetic particles 511 are to be immobilized, a Au film is deposited as a fixed film 510. Then, in order to detect a magnetic particle, a voltage is applied to the upper electrode 508 and the lower electrode 501, and a current having a desired magnitude is permitted to flow across them. In this embodiment, a current having a desired magnitude is one in that, in consonance with the inversion of magnetization, a change in the resistance occurs in the TMR film whereon magnetic particles are not immobilized, while such a change does not occur in a TMR film whereat magnetic particles are immobilized.

Figure 6:
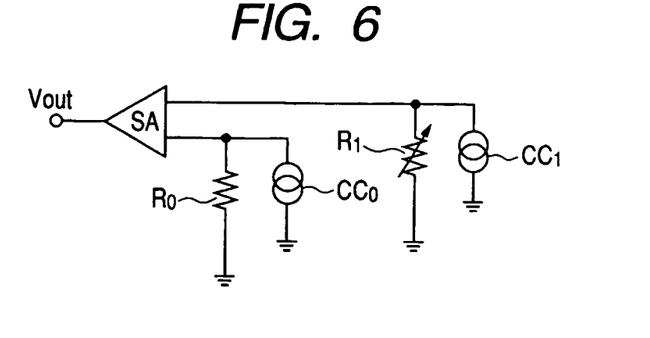
FIG. 6 is a diagram for explaining the circuit arrangement of a magnetic material sensor according to a first embodiment of the present invention.

FIG. 6 is a diagram for explaining the circuit structure of the magnetic material sensor according to this embodiment. A TMR film $R_1$ having the above structure, and a constant current source $CC_1$, for supplying a current to the TMR film $R_1$, are connected to one of the input terminals of a sense amplifier SA. A TMR film $R_0$, whereon magnetic particles are not immobilized, i.e., a Au film is not deposited on the top, and a constant current source $CC_0$, for supplying a current to the TMR film $R_0$, are connected to the other input terminal. The sizes of the two TMR films are 150 nm×65 nm, and easy axes of magnetization are present longitudinally. It is assumed that the magnitude of a current to be supplied by the constant current source $CC_1$ is equal to the magnitude of a current to be supplied by the constant current source $CC_0$.

Before the detection process, the magnetization directions of the detection layer and the magnetized pinned layer should be parallel. In this embodiment, a magnetic field may be applied either externally or by spin injection. During the detection process, electrons are injected from the detection layer side of the TMR film $R_0$ and the TMR film $R_1$. When magnetic particles are immobilized on the top of the TMR film $R_1$, the magnetization direction of the TMR film $R_1$ is not inverted, and the resistance of the TMR film $R_1$ becomes lower than the resistance of the TMR film $R_0$. The difference in the resistances is detected as a difference in the voltages. And when magnetic particles are not immobilized on the top of the TMR film $R_1$, the resistances of the TMR films $R_0$ and $R_1$ are equal and there is no difference in the voltages.

In this embodiment, magnetic particles on the surfaces that are to be detected are covered with SiO$_2$, and are coupled with the SH group by causing a reaction with mercaptosilanol in an acetate solution. Thus, when a solution containing these magnetic particles is dropped onto the surface of the detector, the thiol group is coupled with the Au film on the top of the magnetoresistive effect film, so that the magnetic particles on the top of the magnetoresistive effect film are immobilized. The diameter of a magnetic particle including the SiO$_2$ film is about 100 nm.

In this embodiment, an explanation has been given for a case wherein the initial magnetization is the parallel state, and a current having a desired magnitude is supplied from the magnetized pinned layer side. However, the initial magnetization may be the antiparallel state, and a current may be supplied from the detection layer side. Or, instead of a constant current, the magnitude of a current to be supplied may be gradually increased.

SECOND EMBODIMENT

In the first embodiment, the rectangular TMR film that employs in-plane magnetized films has been used as a magnetic material sensor. However, the magnetic material sensor of this invention can be provided by employing perpendicular magnetized films.

Figure 7:
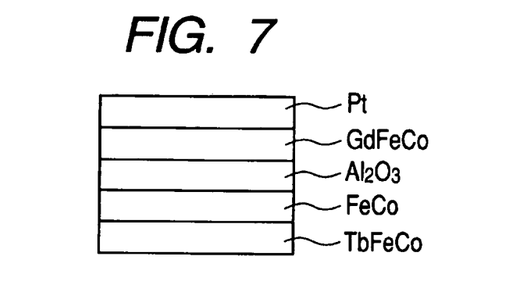
FIG. 7 is a schematic diagram showing the structure of a magnetoresistive effect film used for a magnetic material sensor according to a second embodiment of the present invention.

In a second embodiment, an example for detecting small magnetic particles having a particle size of 50 nm will be explained. As in the first embodiment, a magnetic particle to be detected is coupled with the SH group, and a Au film is formed on the top of a magnetoresistive effect film. The circuit of a magnetic material sensor is the same as that in the first embodiment and the magnetoresistive effect film is a TMR film that, as shown in FIG. 7, is formed by laminating a TbFeCo alloy film, a FeCo alloy film, a Al$_2$O$_3$ film, a GdFeCo Alloy film and a Pt film in the named order. The TbFeCo alloy film is a perpendicular magnetized film having a composition that is superior in magnetization to the auxiliary lattice of a transition metal, and that is similar to a compensation composition. The TbfeCo alloy film and the FeCo alloy film are exchange-coupled, and the magnetization direction of the FeCo alloy film is aligned with the perpendicular direction. That is, the exchange coupling film formed using the TbFeCo alloy film and the FeCo alloy film serves as a magnetized pinned layer. The GdFeCo alloy film is a detection layer, and as does the TbFeCo alloy film, has a composition superior in magnetization to the auxiliary lattice of a transition metal, and the magnetization direction thereof is aligned with the perpendicular direction. The size of the TMR film is 65 nm×65 nm.

In the initial state before detection, the magnetization directions of the magnetized pinned layer and the detection layer are set antiparallel. During the detection process, a detection current is supplied for the injection of electrons from the magnetized pinned layer side. Regardless of the presence/absence of a magnetic particle, the detection current is gradually increased until the current value is reached at which the magnetization of the detection layer is inverted. When magnetic particles are immobilized on a TMR film $R_1$ on which the Au film is deposited, the resistance of the TMR film $R_1$ is lowered to a specified current value, while a high resistance is maintained for a TMR film $R_0$, so that a voltage difference occurs between the voltages of the two TMR films. And when the value of the current is further increased, there is a comparative reduction in the resistance of the TMR film $R_0$ that is continued until the voltages of the two TMR films are equal.

When magnetic particles are not immobilized on the top of the TMR film $R_1$, the resistances of the TMR films $R_1$ and $R_0$ are changed at the same time, and a difference in the voltages is not detected.

In this embodiment, an explanation has been given for a case wherein the initial magnetized state is antiparallel and wherein a current is so supplied from the detection layer side that it is gradually increased. However, the initial magnetized state may be parallel, and a current may be supplied by the magnetized pinned layer side, or the magnitude of the current may be a constant.

THIRD EMBODIMENT

The magnetic material sensor of this invention can also be employed as a biosensor. In a third embodiment, an explanation will be given for a biosensor that detects a prostate specific antigen (PSA) that is known as a marker for prostate cancer.

A magnetoresistive effect film used for this embodiment has the same structure as the TMR film used for the first embodiment, and the particle size of a magnetic particle is about 100 nm.

In order to hold the primary antibody on the surface of an Au film that is deposited on the magnetoresistive effect film, the surface of the Au film is treated with a piranha solution (sulfuric acid:hydrogen peroxide=3:1), and is thereafter treated with a 1 mM ethanol solution of 10-carboxy-1-decanthiol. As a result, a self-organizing film (SAM) wherein a carboxyl group is represented is deposited on the surface. Furthermore, in order to immobilize the primary antibody, a soluble carbodiimide (WSC) and a N-hydroxysuccinimide react with each other to transform the carboxyl group on the surface of the Au film into an active ester group. This transformation can be confirmed, for example, using the absorbed total reflection measurement method (ATR). Then, by bringing into contact an anti-PSA antibody, the amino group of the antibody is coupled with the SAM, and the primary antibody is immobilized. This pinned can be confirmed when amido coupling derived from the antibody is detected by the ATR. After the antibody has been immobilized, the surface of the Au film is treated with ethanol amine, at a high density, to block the active ester group that does not react. Through the process described above, a detection sensor can be constructed wherein the anti-PSA antibody, as the primary antibody, is immobilized.

According to the following protocol, this detection sensor can be employed to attempt the detection of a prostate specific antigen (PSA) that is known as a marker for prostate cancer. The primary antibodies that recognize the PSAs are immobilized to the detection sensor.

(1) The detection sensor is immersed in a phosphate buffer physiological saline solution (sample solution) containing PSAs that serve as samples, and is incubated for five minutes.

(2) The PSAs that do not react are removed from the detection sensor using a phosphate buffer physiological saline solution.

(3) The detection sensor, once it has gone through the processes (1) and (2), is immersed in a phosphate buffer physiological saline solution that contains anti-PSA antibodies (secondary antibodies) marked by magnetic particles, and is incubated for five minutes.

(4) The marker antibodies that did not react are then removed using a phosphate buffer physiological saline solution.

Figure 8:
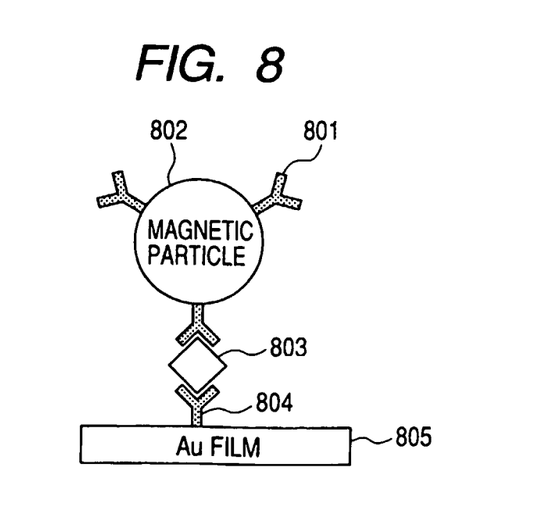
FIG. 8 is a schematic conceptual diagram showing the state of a biosensor according to a third embodiment of the present invention wherein a magnetic particle is immobilized.

By following this protocol, as shown in FIG. 8, secondary antibodies 801, an antigen 803 and a primary antibody 804 are coupled together, and a magnetic particle 802 is immobilized on the top of a Au film 805 that serves as a magnetoresistive effect film. That is, when the antigen 803 is not present in a sample, the magnetic particle 802 is not immobilized on the magnetoresistive effect film, and only whether the magnetic particle 802 is present or absent need be detected for the antigen 803 to be detected. Further, when the number of the immobilized magnetic particles 802 is detected, the quantity of the antigens 803 contained in the sample can also be indirectly obtained.

The magnetic material sensor according to the present invention can detect a magnetic material without applying a magnetic field to magnetic particles. Further, even a finely structured sensor can enable the detection of a magnetic material without the consumption of a large amount of energy being required. In addition, through the modification of a magnetic material, the magnetic material sensor of this invention can also be used for the detection of a biomaterial.

This application claims priority from Japanese Patent Application No. 2005-023518 filed Jan. 31, 2005, which is hereby incorporated by reference herein.

The invention claimed is:

1. A magnetic sensor comprising:
a magnetoresistive effect film;
a current source for supplying a spin-polarized current to the magnetoresistive effect film; and
a detector for detecting whether a magnetic material is present or not, or for detecting a number of magnetic particles,
wherein the magnetoresistive effect film comprises:
a detection layer comprising a magnetic film, the magnetization direction of which is changed by perpendicularly supplying the spin-polarized current from the current source to the magnetoresistive effect film;
a magnetized pinned layer comprising a magnetic film, the magnetization direction of which is not changed by the perpendicularly supplying of the spin-polarized current from the current source to the magnetoresistive effect film; and
a non-magnetic film, which is formed between the detection layer and the magnetized pinned layer,
wherein the detection layer is thinner than the magnetized pinned layer, the thickness of said detection layer is smaller than a spin diffusion length, and the thickness of said pinned layer is larger than the spin diffusion length, and
wherein an electron of the spin-polarized current is supplied from a side of the detection layer.

2. A magnetic sensor according to claim 1, wherein a change in the magnetization direction of the detection layer differs depending on a floating magnetic field generated by a magnetic material to be detected.

3. A magnetic sensor according to claim 1, further comprising:
a magnetoresistive effect film that does not interact with a magnetic material to be detected,
wherein the detector employs, as a reference voltage, a voltage obtained by the magnetoresistive effect film that does not interact with the magnetic material to be detected.

4. A detection method, for employing a magnetic sensor that includes a magnetoresistive effect, comprising the steps of:
supplying a spin-polarized current to the magnetoresistive effect film; and
detecting a change in resistance at the magnetoresistive effect film to determine whether a magnetic material is present or not, or to determine a number of magnetic particles,
wherein the magnetoresistive effect film comprises:
a detection layer comprising a magnetic film, the magnetization direction of which is changed by perpendicularly supplying the spin-polarized current to the magnetoresistive effect film;
a magnetized pinned layer comprising a magnetic film, the magnetization direction of which is not changed by the perpendicularly supplying of the spin-polarized current; and
a non-magnetic film, which is formed between the detection layer and the magnetized pinned layer,
wherein the detection layer is thinner than the magnetized pinned layer, the thickness of said detection layer is smaller than a spin diffusion length, and the thickness of said pinned layer is larger than the spin diffusion length, and
wherein an electron of the spin-polarized current is supplied from a side of the detection layer.

5. A detection method according to claim 4, further comprising the steps of:
setting to parallel magnetization directions the detection layer and the magnetized pinned layer;

supplying a current from a magnetized pinned layer side to a detection layer side so as to increase a current value as time elapses; and detecting for the magnetoresistive effect film a resistance change, so as to determine a presence or an absence of magnetic particles, or a number of magnetic particles.

6. A detection method according to claim 4, further comprising the steps of:

setting to antiparallel magnetization directions the detection layer and the magnetized pinned layer;

supplying a current from a detection layer side to a magnetized pinned layer side so as to increase a current value as time elapses; and detecting for the magnetoresistive effect film a resistance change, so as to determine the presence or the absence of magnetic particles, or the number of magnetic particles.

7. A detection method according to claim 4, further comprising the steps of:

when there is no interaction between a magnetic material to be detected and the detection layer, supplying, from the magnetized pinned layer side to the detection layer side, a current of such a magnitude that a magnetized state is changed, or supplying, when there is an interaction, a current of such a magnitude that the magnetized state is changed, but the change when there is an interaction is less than the change when there is no interaction; and detecting a change in a resistance of the magnetoresistive effect film so as to determine a presence or an absence of magnetic particles, or a number of magnetic particles.

8. A detection method according to claim 4, whereby a voltage, obtained by the magnetoresistive effect film, that does not interact with a magnetic material to be detected is employed as a reference voltage, and a presence or an absence of a magnetic material, or a number of magnetic particles, is detected by employing the reference voltage.

9. A target material detection sensor wherein magnetic particles are immobilized, through a target material to be detected, on one part of a magnetic material sensor according to claim 1 in order to detect the target material.

10. A target material detection kit comprising:

a target material detection sensor according to claim 9; and magnetic particles modified by a material so as to be specifically coupled with a target material.

* * * * *